US006531159B1

(12) United States Patent
Masuko et al.

(10) Patent No.: US 6,531,159 B1
(45) Date of Patent: Mar. 11, 2003

(54) MATERIALS ELIMINATING CANNABINOIDS AND COLUMNS FOR THE ELIMINATION OF CANNABINOIDS WITH THE USE OF THE SAME

(75) Inventors: Sanae Masuko, Kusatsu (JP); Akira Yokoyama, Kawasaki (JP); Kazuhiro Moriyama, Toride (JP); Ikuro Maruyama, Kagoshima (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 09/720,303

(22) PCT Filed: Apr. 26, 2000

(86) PCT No.: PCT/JP00/02716

§ 371 (c)(1),
(2), (4) Date: Dec. 26, 2000

(87) PCT Pub. No.: WO00/66260

PCT Pub. Date: Nov. 9, 2000

(30) Foreign Application Priority Data

Apr. 28, 1999 (JP) ............................................. 11-121555

(51) Int. Cl.⁷ ................................................. A61K 9/14

(52) U.S. Cl. ....................... 424/489; 424/484; 424/486; 424/501; 424/443

(58) Field of Search ................................. 424/489, 484, 424/486, 443, 501

(56) References Cited

U.S. PATENT DOCUMENTS

| 4,375,414 | A |   | 3/1983  | Strahilvetiz ................. 210/638 |
| 4,650,784 | A |   | 3/1987  | Ramsden et al. ............ 502/407 |
| 4,680,120 | A |   | 7/1987  | Ramsden et al. ........... 210/635 |
| 4,680,121 | A |   | 7/1987  | Ramsden et al. ........... 210/635 |
| 4,690,907 | A | * | 9/1987  | Hibino et al. ................ 436/514 |
| 5,137,626 | A |   | 8/1992  | Parry et al. .............. 210/198.2 |
| 5,532,237 | A |   | 7/1996  | Gallant et al. ........... 514/235.2 |
| 5,817,766 | A | * | 10/1998 | Hui et al. ................. 530/387.1 |
| 5,874,459 | A |   | 2/1999  | Makriyannis et al. ....... 514/425 |
| 6,022,693 | A | * | 2/2000  | Baumgartner ............... 435/7.1 |

FOREIGN PATENT DOCUMENTS

| EP | 658546   | 6/1995 |
| WO | 96/18600 | 6/1996 |
| WO | 99/02499 | 1/1999 |

\* cited by examiner

Primary Examiner—Thurman K. Page
Assistant Examiner—Liliana Di Nola-Baron
(74) Attorney, Agent, or Firm—Nixon & Vanderhye P.C.

(57) ABSTRACT

The present invention provides (1) a removal material for cannabinoids present in body fluids where at least one substance from amongst substances with functional groups capable of hydrogen bonding, substances with hydrophobic functional groups, substances having cationic functional groups and physiologically active substances, is immobilized on a water-insoluble carrier, and (2) a cannabinoid removal column characterized in that it incorporates an aforesaid material (1). In accordance with the present invention, cannabinoids present in, for example, the blood, can be selectively removed.

14 Claims, No Drawings

MATERIALS ELIMINATING CANNABINOIDS AND COLUMNS FOR THE ELIMINATION OF CANNABINOIDS WITH THE USE OF THE SAME

This application is a 371 of PCT/JP00/02716 filed Apr. 26, 2000.

TECHNICAL FIELD

The present invention relates to a cannabinoid removal material and to a cannabinoid removal column in which this is employed. In particular, by enabling cannabinoids to be eliminated from human blood, the invention is suitably employed in applications to ameliorate sepsis and other such medical conditions, or in applications to ameliorate symptoms of hypotension brought about by raised cannabinoid concentrations in the blood of 500 pg/ml or above, and especially 1 ng/ml or above.

PRIOR ART

It has become clear that cannabinoids, which may be termed endogenous marihuana, can be induced/expressed by means of lipopolysaccharide (hereinafter abbreviated to LPS). Cannabinoids are said to cause psychoneural symptoms (consciousness modification, etc) via CB1 receptors expressed in the brain, and also to cause hypotension and immunodeficiency via CB1 and CB2 expressed peripherally. A recent publication (The FASEB Journal, Vol.28: 1035 1998) describes the fact that LPS, by acting on platelets and macrophages, brings about expression and release of 2-arachidonylglycerol and anandamide, which are respectively types of cannabinoid, and these bring about hypotensive shock. Furthermore, in a rat endotoxaemia model, it has been shown that hypotensive shock can be prevented by blocking cannabinoids based on CB1 receptor antagonists. For these reasons, it can be concluded that cannabinoids play an important role in endotoxin shock.

Consequently, the removal of cannabinoids can be expected to be effective in the amelioration of hypotensive shock produced by cannabinoids.

The present invention has as its objective to provide a material for removing the cannabinoids which cause such hypotension and immunodeficiency, etc, together with a removal column wherein this material is employed.

DISCLOSURE OF THE INVENTION

To resolve the aforementioned problem, the present invention has the following constitution:

A material for the removal of cannabinoids in body fluids where there is immobilized on a water-insoluble carrier a substance with functional groups capable of hydrogen bonding, for example a substance having cationic functional groups and/or a physiologically active substance, and preferably a substance also having hydrophobic groups; and a cannabinoid removal column which is characterized in that it incorporates said removal material.

OPTIMUM FORM FOR PRACTISING THE INVENTION

The present invention offers a material enabling cannabinoids to be removed. In the present invention, the term cannabinoids refers to generally known cannabinoids and denotes substances capable of bonding with cannabinoid receptors (CB1 and CB2), including marihuana-derived cannabinoids and endogenous cannabinoids. While there are no particular restrictions, there can be cited as examples anandamide (arachidonylethanolamide), 2-arachidonylglycerol (hereinafter abbreviated to 2-AG), cannabinol, cannabidiol, Δ9-tetrahydrocannabinol, levonantranol, nabilone, 6-S-[3(R),6α,6aα,9α,10aβ]-(−)-5, 6,6a,7,8,9,10,10a-octahydro-6-methyl-3-(1-methyl-4-phenylbutoxy)-1,9-phenanthridinediol 1-acetate hydrochloride and R-(+)-(2,3-hydro-5-methyl-3-[4-morponolinylmethyl]pyrrole[1,2,3-de]-1,4-benzoxalin-6-yl (1-naphthalenyl)naphthanone mono-methanesulphonate. Furthermore, cells incorporating cannabinoids, for example, platelets and macrophages, etc, are also included. Again, cannabinoids bound to lipid, albumin and other such serum components are included.

As examples of lipids which bind cannabinoids there are simple lipids, which are merely the esters of alcohols and fatty acids, and complex lipids comprising phospholipids, lipoproteins (chylomicrons, VLDL, LDL, HDL, VHDL), and the like.

As examples in the present invention of the functional groups capable of hydrogen bonding, there are cationic functional groups, carboxyl groups, sulphate ester groups, sulphonic acid groups, phosphoric acid groups, hydroxyl groups, thiol groups, aldehyde groups, carbonyl groups, urea bonds, thiourea bonds and the like.

As examples of cationic functional groups, there are primary amino groups, secondary amino groups, tertiary amino groups, imino groups, quaternary ammonium groups, amide groups and the like.

As examples of hydrophobic functional groups, there are alkyl groups, aromatic groups and the like.

Synthetic polymers such as polystyrene, polypropylene, polyamide, polyimide, poly(aromatic vinyl compounds), polyester, polymethyl methacrylate, polysulfone, polyethylene, polyvinyl alcohol, polytetrafluoroethylene and the like, and natural polymers including cellulose, collagen, chitin, chitosan, dextran and derivatives thereof, are suitably used as the insoluble carrier material employed in the present invention. Furthermore, materials comprising a metal, ceramic, glass or other such inorganic material coated with a suitable polymer and where the surface has been directly modified, are also suitably used.

The material of the present invention may have the form of fibre, hollow fibre, beads, flat film or powder, etc, but a fibre, hollow fibre or bead-form material suitable for the extracorporeal circulation of whole blood, which is circulated in a column without separating the blood corpuscles and plasma, is particularly preferred. To increase the percentage adsorption, a porous material of large contact area is preferred. Furthermore, in the case of beads, these should show little pressure loss when packed in a column and have a large surface area, so beads of diameter in the range 50–1000 μm are preferred, with a diameter in the range 200–700 μm being further preferred.

There are no particular restrictions on the components of a fibre material but polystyrene fibre, crosslinked polystyrene fibre, acrylic acid/acrylonitrile copolymer fibre or carboxyl group-containing polyvinyl alcohol fibre is preferably used, in that the introduction of functional groups is particularly easy. Furthermore, from the point of view of processability and durability, so-called islands-in-a-sea type fibre, where reinforcement is effected by the islands component, is preferably used, for example islands-in-a-sea type fibre employing polystyrene as the sea component and polypropylene or the like as the islands component.

Regarding the surface area of the fibre material, on the assumption that it is to be used in extracorporeal circulation a material having a surface area in the range 0.1–100 m²/g is preferred. The surface area is measured by the BET method.

Reference to a physiologically active substance in the present invention means a polypeptide, polysaccharide, nucleic acid or the like and specific examples are polymyxin, vancomycin, actinomysin, viomysin, albumin and protein A, etc. Polymyxin is an antibiotic produced by Bacillus polymyxa, and there are types such as polymyxin A, polymyxin B, polymyxin D and polymyxin E. It has an antimicrobial action against gram-negative bacteria.

The cannabinoid adsorption is strongly influenced by the cannabinoid concentration and by the proportions of the carrier to cannabinoid solution. The cannabinoid adsorption is expressed by the percentage adsorption, in terms of 50 mg of fibre-form material or 200 µl of bead-form material, when reaction is carried out at 37° C. for 2 hours with 1 ml of normal human serum to which a 1 µg/ml concentration of cannabinoid is added. To determine the percentage cannabinoid adsorption, either the cannabinoid which has been adsorbed onto the carrier is measured after elution from the carrier, or the cannabinoid remaining in the serum is measured. As a result, based on 50 mg of material in the form of fibre or 200 µl in the form of beads, materials which adsorb and remove at least 200 ng (20%) of the cannabinoid are preferred, and those which adsorb and remove at least 300 ng (30%) of the cannabinoid are further preferred.

Cannabinoid can be removed by passing a treatment liquid containing the cannabinoid through a column packed with the above-mentioned cannabinoids removal material. As the treatment liquid, there is used blood, plasma or the like, in which cannabinoid is present. Regarding the method of removal, in the case of a column where, for example, the material of the present invention has the form of a fabric and is packed into the column wound around a central axis, a method of removing the cannabinoid by introducing the treatment liquid containing the cannabinoid into the central axis interior and causing it to flow out from holes formed in the central axis to the outside is preferred in terms of efficient adsorption of the cannabinoid.

The material of the present invention can favourably eliminate cannabinoids and it can be suitably employed in applications like the amelioration of reduced blood pressure by use in extracorporeal circulation, etc, in the case of patients showing symptoms of hypotension where cannabinoid blood concentrations are 500 pg or more, in particular 1.0 ng/ml or more.

EXAMPLES

Below, a detailed investigation is included using examples, but the content of the invention is not to be restricted by these examples. The method of measuring the percentage cannabinoid adsorption is given below. Anandamide and 2-arachidonylglycerol (hereinafter abbreviated to 2-AG) were used as the cannabinoids in all the examples.

Using 50 mg of the material when in fibre-form and 200 µl when in the form of beads, reaction was carried out at 37° C. for 2 hours with 1 ml of normal human serum to which anandamide or 2-AG had been added at a concentration of 1 µg/ml, and the carrier then washed thoroughly with physiological saline. Thereafter, the water component was fully eliminated and immersion performed for 1 hour at room temperature in 500 µl of ethanol in the case of fibre-form material or 1.8 ml of ethanol in the case of beads, and the anandamide or 2-AG eluted. 20 µl of this ethanol solution was analysed by reverse-phase high performance liquid chromatography (HPLC). The column used was a Tosoh Corporation TSK-GEL ODS-80TM (4.6 mm ID×15 cm) column, and the solvent employed was an acetonitrile:8.5% $H_3PO_4$=9:1 solution. Elution was carried out at a flow rate of 1 ml/minute and the anandamide or 2-AG peak area was compared with standard anandamide or 2-AG peak areas, and the quantity of anandamide or 2-AG in the liquid eluted from the carrier calculated.

When the concentration was low, drying down to a solid was carried out using a vacuum-type centrifuge, then dissolution again performed in a small amount of ethanol and analysis carried out by HPLC. For example, when beads were used, 1 ml of ethanol elution liquid was dried down to a solid, then dissolution in 200 µl of ethanol performed and 20 µl analysed by HPLC.

Example 1

Adsorption by a Carrier on which a Physiologically Active Substance has been Immobilized 50 g of an islands-in-a-sea type composite fibre (number of islands 16, fibre fineness 2.6 denier, tensile strength 2.9 g/d, elongation 50%, number of filaments 42), in which the islands component comprised 50 parts by weight of polypropylene (Mitsui "Nobrene" J3HG) and the sea component comprised a mixture of 46 parts by weight of polystyrene ("Styron" 666) and 4 parts by weight of polypropylene (Sumitomo "Nobrene" WF-727-F), was immersed in a mixed solution consisting of 113 g of N-methylol-α-chloroacetamide, 750 g of nitrobenzene, 750 g of 98% sulphuric acid and 1.61 g of paraformaldehyde, and reaction carried out at 10° C. for 2 hours. After removing the fibre from the reaction liquid and washing with 1300 g of nitrobenzene, it was then washed with 1000 ml of water and neutralization carried out with 31.3 ml of 25% NaOH solution. Next, the fibre was washed with 1250 ml of methanol and, finally, washing with warm water was performed.

To the chloroacetamidomethylated fibre thus obtained, a solution formed by dissolving 1.25 g of polymyxin B (produced by DUMEX) in 800 ml of water was added, together with 31.1 ml of 0.1 N NaOH, then shaking carried out for 1 hour and the immobilization reaction performed. After washing the reacted fibre three times with 800 ml of 0.077 N hydrochloric acid, washing was carried out three times with 800 ml of water and fibre-immobilized polymyxin was obtained. The amount of immobilized polymyxin was found to be 6 mg/g by a method of amino acid analysis.

The fibre thus obtained was steam-sterilized, cut to 50 mg, and then the percentage anandamide or 2-AG adsorption was calculated in accordance with the aforementioned method of measuring percentage cannabinoid adsorption.

Anandamide or 2-AG present in the serum was well adsorbed and removed by means of a carrier on which a physiologically active substance had been immobilized.

Example 2

Adsorption by means of Hydrophobic Carriers Possessing Functional Groups Capable of Hydrogen Bonding and Functional Groups with 10 or more Carbons Using, in each case, 200 µl of crosslinked agarose beads having alkyl groups represented by —$C_5H_{11}$, —$C_8H_{17}$, —$C_{10}H_{21}$ or —$C_{12}H_{25}$, or 50 mg of polyethylene terephthalate (hereinafter just referred to as polyester) fibre, the percentage anandamide or 2-AG adsorption was calculated in accordance with the aforementioned method of measuring percentage cannabinoid adsorption.

Anandamide or 2-AG present in the serum was well adsorbed and remove d by means of the hydrophobic carriers possessing functional groups capable of hydrogen bonding and alkyl groups with ten or more carbons.

Example 3

Adsorption by a Fibre-form Carrier Containing Amino Groups, Urea Bonds and Aromatic Rings 50 g of an islands-in-a-sea type composite fibre as described in U.S. Pat. No. 4,661,260 (fineness 2.6 denier, number of islands 16) comprising 50 parts by weight of sea component (a mixture of 46 parts by weight of polystyrene and 4 parts by weight of polypropylene) and 50 parts by weight of islands component (polypropylene) was reacted at 20° C. for 1 hour with a mixed solution of 50 g of N-methylol-α-chloroacetamide, 400 g of nitrobenzene, 400 g of 98% sulphuric acid and 0.85 g of paraformaldehyde. The fibre was then washed with nitrobenzene, and reaction halted by insertion into water. Thereafter, the fibre was further washed with methanol and with warm water, and chloroacetamidomethylated crosslinked polystyrene fibre (hereinafter abbreviated to AMPSt fibre) obtained.

0.9 g of tetraethylenepentamine was dissolved in 50 ml of DMF, and 1 g of the AMPSt fibre (corresponding to a chloro content of 2 mmol) was added to this solution while stirring. Reaction was carried out at 25° C. for 6 hours. Subsequently, the AMPSt fibre was washed using 200 ml of DMF on a glass filter, and then added to a solution consisting of 50 ml of DMF in which 1 g of 4-chlorophenyl isocyanate had been dissolved, and reaction carried out at 25° C. for 1 hour. Thereafter, the fibre was washed on a glass filter using 200 ml of DMF and 200 ml of distilled water. The adsorbent fibre obtained (which contained amino groups, urea bonds and aromatic rings) was cut to a weight of 50 mg, and the percentage anandamide or 2-AG adsorption calculated in accordance with the aforementioned method of measuring percentage cannabinoid adsorption.

Anandamide or 2-AG present in the serum was well adsorbed and removed by means of the carrier with hydrophobic functional groups which, although the number of carbons therein was six, corresponded to ten carbons in that the halogen corresponded to four carbons in terms of its hydrophobic character.

Example 4

Adsorption by a Fibre-form Carrier having Amino Groups and Alkyl Groups

After cooling a mixed solution of 16 ml of nitrobenzene and 32 ml of sulphuric acid to 0° C., 4.2 g of N-methylol-α-chloroacetamide was added and dissolved and, while well-stirring, this was added to 3 litres of a nitrobenzene solution of Udel polysulfone P3500 (300 g per 3 litres) at 10° C. Further stirring was carried out at room temperature for 3 hours. Thereafter, the reaction mixture was introduced into a large excess of cold methanol and the polymer precipitated. After thoroughly washing the precipitate with methanol, it was dried and then reprecipitated from dimethylformamide/methanol, to give 303 g of α-chloroacetamidomethylated polysulfone (substitution factor 0.05; polymer-C).

Next, 33 ml of lauryl bromide (a molar proportion of 0.1 based on that of polyethyleneimine) was added to a solution formed by dissolving 60 g of polyethyleneimine (average molecular weight 10,000: Wako Pure Chemical Industries Ltd) in 300 ml of dimethylformamide and, after heating at 60° C. for 6 hours, this was mixed with 300 ml of a dimethylformamide solution containing 30 g of the aforementioned polymer-C and stirring carried out at room temperature for 24 hours. To this was added 160 ml (a molar proportion of 0.5) of lauryl bromide and further stirring was carried out at room temperature for 48 hours. The reaction mixture was then added to a large excess of methanol and the polymer which precipitated was filtered off. The polymer obtained was dried and on reprecipitating from dimethylformamide/methanol, 27 g of polysulfone-immobilized N-alkylated polyalkyleneimine was prepared.

20 g of a nylon 66 fibre wad of fibre fineness 1 denier was immersed in a solution comprising 250 ml of methylene chloride containing 5 g of the aforesaid adsorbent of the present invention and, after 20 hours, the fibre was removed and, having squeezed-out the liquid, the fibre was air-dried and 23 g of coated fibre obtained. This was cut to a weight of 50 mg and the percentage anandamide or 2-AG adsorption calculated in accordance with the aforementioned method of measuring percentage cannabinoid adsorption.

Anandamide or 2-AG present in the serum was well adsorbed/removed by means of the hydrophobic carrier possessing amino groups and $C_{12}$ alkyl groups.

Example 5

Adsorption by a Carrier having Cationic and Hydrophobic Functional Groups 50 g of an islands-in-a-sea type composite fibre (number of islands 16, fibre fineness 2.6 denier, tensile strength 2.9 g/d, elongation 50%, number of filaments 42), in which the islands component comprised 50 parts by weight of polypropylene (Mitsui "Nobrene" J3HG) and the sea component comprised a mixture of 46 parts by weight of polystyrene ("Styron" 666) and 4 parts by weight of polypropylene (Sumitomo "Nobrene" WF-727-F), was immersed in a mixed solution consisting of 113 g of N-methylol-a-chloroacetamide, 750 g of nitrobenzene, 750 g of 98% sulphuric acid and 1.61 g of paraformaldehyde, and reaction carried out at 10° C. for 2 hours. The fibre was then removed from the reaction liquid and, after washing with 1300 g of nitrobenzene, it was washed with 1000 ml of water and neutralization performed with 31.3 ml of 25% NaOH solution. This fibre was then washed with 1250 ml of methanol and, finally, washing with warm water was performed, and chloroacetamidomethylated crosslinked polystyrene fibre obtained. The fibre was hydrolysed and, using a 50 mg cut portion of this fibre with benzylamino groups (cationic and hydrophobic functional groups), and also separately using 200 μl of dextran sulphate beads with anionic functional groups, the percentage anandamide or 2-AG adsorption in each case was calculated in accordance with the aforementioned method of measuring percentage cannabinoid adsorption.

Anandamide or 2-AG present in the serum was well adsorbed and removed by means of the carrier possessing cationic and hydro phobic functional groups.

TABLE 1

| | Carrier with Functional Groups Capable of Hydrogen Bonding | | Anandamide Adsorption (%) | 2-AG Adsorption (%) |
|---|---|---|---|---|
| Example 1 | fibre-immobilized polymyxin B | physiologically active substance | 44.0 | 35.2 |
| Example 2 | agarose-$C_5H_{11}$ | contains hydrophobic functional groups | 6.4 | 5.3 |
| | agarose-$C_8H_{17}$ | | 7.0 | 6.2 |
| | agarose-$C_{10}H_{21}$ | | 39.5 | 35.4 |
| | agarose-$C_{12}H_{25}$ | | 35.3 | 36.7 |
| | polyester fibre | | 10.5 | 7.8 |
| Example 3 | fibre containing amino groups + aromatic rings + urea bonds | | 41.1 | 39.5 |
| Example 4 | amino groups + alkyl groups ($C_{12}$) | | 29.2 | 26.5 |
| Example 5 | fibre containing benzylamino groups | contains cationic and hydrophobic functional groups | 97.9 | 88.2 |
| | dextran sulphate | contains anionic and hydrophilic functional groups | 5.0 | 6.5 |

Example 6

Using 50, 100 and 200 mg of the carrier fibre employed in Example 1, on which a physiologically active substance had been immobilized, the percentage adsorption from 2 ml of serum to which 1 μg of anandamide had been added was calculated in each case in accordance with the aforesaid method of measuring percentage cannabinoid adsorption.

The amounts of anandamide adsorbed and removed from the serum by the carrier on which the physiologically active substance had been immobilized increased as the amount of carrier increased.

TABLE 2

| Amount of Carrier (mg) | Anandamide Adsorption (%) |
|---|---|
| 50 | 44.0 |
| 100 | 63.9 |
| 200 | 88.8 |

Example 7

Anandamide was added to normal human serum and to serum from which lipid had been removed and, using 50 mg of the fibre employed in Example 1, the percentage anandamide adsorption was calculated in accordance with the aforesaid method of measuring percentage cannabinoid adsorption.

The percentage anandamide adsorption from the normal serum was higher than that from the serum from which lipid had been removed and, as a result of fractionating the lipids present in the serum by density gradient centrifugation, anandamide was detected in the LDL, HDL and VHDL fractions in the proportions 1:3.4:8.2. This again indicates that the percentage anandamide adsorption is high with carriers of high percentage lipid adsorption.

TABLE 3

| | Anandamide Adsorption (%) |
|---|---|
| Normal serum | 97.4 |
| Serum with lipid removed | 64.1 |

Industrial Application Potential

By means of the present invention, there can be provided a material for removing cannabinoids.

What is claimed is:

1. A cannabinoid removal material for removing cannabinoids from body fluids, said material, comprising functional groups capable of hydrogen bonding and hydrophobic functional groups immobilized on a water-insoluble carrier, wherein the hydrophobic functional groups are alkyl groups with 10 or more carbon atoms.

2. A cannabinoid removal material according to claim 1 where the water-insoluble carrier is a material with urea bonds and/or thiourea bonds.

3. A cannabinoid removal material according to claim 1 where the removal material absorbs at least 30% lipid.

4. A cannabinoid removal material according to claim 1 where the removal material absorbs at least 30% lipid and the percentage cannabinoid adsorption is at least 20%.

5. A cannabinoid removal material according to claim 4 where the percentage lipid adsorption is at least 30% and the percentage cannabinoid adsorption is at least 30%.

6. A cannabinoid removal material according to claim 1 where the water-insoluble carrier has a fibrous form.

7. A cannabinoid removal material according to claim 1 where the water-insoluble carrier has the form of beads.

8. A cannabinoid removal material according to claim 6 where said fibrous carrier is selected from polystyrene fiber, crosslinked polystyrene fiber, acrylic acid/acrylonitrile copolymer fiber and carboxyl group-containing polyvinyl alcohol fiber.

9. A cannabinoid removal material according to claim 6 where the fibrous carrier comprises fiber with an islands-in-a-sea structure.

10. A cannabinoid removal column which incorporates a cannabinoid removal material according to claim 1.

11. A method of treating sepsis comprising contacting a body fluid with the cannabinoid removal material, said material comprising functional groups capable of hydrogen bonding and hydrophobic functional groups immobilized on a water-insoluble carrier, wherein the hydrophobic functional groups are alkyl groups with 10 or more carbon atoms.

12. A method according to claim 11 where the body fluid is blood or plasma.

13. A method of treating sepsis comprising passing a body fluid through the column incorporating a cannabinoid material, said material comprising functional groups capable of hydrogen bonding and hydrophobic functional groups immobilized on a water-insoluble carrier, wherein the hydrophobic functional groups are alkyl groups with 10 or more carbon atoms.

14. A method according to claim 13 where the body fluid is blood or plasma.

* * * * *